United States Patent [19]

York et al.

[11] 4,305,866

[45] Dec. 15, 1981

[54] POLYOLEFINS STABILIZED WITH CYCLIC DIPHOSPHITES

[75] Inventors: James F. York, Morgantown, W. Va.; Leo L. Valdiserri, Belpre, Ohio

[73] Assignee: Borg-Warner Chemicals, Inc., Parkersburg, W. Va.

[21] Appl. No.: 70,949

[22] Filed: Aug. 30, 1979

Related U.S. Application Data

[60] Division of Ser. No. 926,485, Jul. 20, 1978, which is a continuation of Ser. No. 663,651, Mar. 4, 1976, abandoned.

[51] Int. Cl.$^3$ .................................................. C08K 5/52
[52] U.S. Cl. ........................... 260/45.7 PH; 260/23 H; 260/45.8 R; 260/45.85 B; 260/927 R
[58] Field of Search ............ 260/45.8 R, 982, 45.7 PH

[56] References Cited

U.S. PATENT DOCUMENTS

| | | | |
|---|---|---|---|
| 2,847,443 | 8/1958 | Hechenbleikner et al. | 260/927 R |
| 3,039,993 | 6/1962 | Friedman | 260/45.7 PH |
| 3,231,531 | 1/1966 | Buckley et al. | 260/23 XA |
| 3,262,896 | 7/1966 | Ackerman | 260/23 XA |
| 3,305,520 | 2/1967 | Fritz et al. | 260/45.7 PH |
| 3,351,683 | 11/1967 | Wu et al. | 260/982 |
| 3,356,770 | 12/1967 | Larrison | 260/982 |
| 3,415,906 | 12/1968 | Shepard et al. | 260/937 |
| 3,502,613 | 3/1970 | Berger | 260/45.8 NT |
| 3,558,554 | 1/1971 | Kuriyama et al. | 260/45.95 B |
| 3,733,296 | 5/1973 | Cleveland et al. | 260/45.7 PH |
| 3,737,485 | 6/1973 | Hechenbleikner | 260/982 |
| 3,922,249 | 11/1975 | Mills | 260/45.8 R |
| 4,221,700 | 9/1980 | Minagawa et al. | 260/45.7 PH |

*Primary Examiner*—John Kight, III
*Assistant Examiner*—R. A. White
*Attorney, Agent, or Firm*—Joseph Shekleton

[57] ABSTRACT

A process for the preparation of mixed aromatic-aliphatic phosphites. The process involves the reaction of an alkylphenol with diphenyl-(or a lower dialkyl-) pentaerythritol diphosphite. The process is simple and inexpensive, and produces a relatively pure product.

8 Claims, No Drawings

POLYOLEFINS STABILIZED WITH CYCLIC DIPHOSPHITES

This application is a divisional of Ser. No. 926,485, filed July 20, 1978, which in turn is a continuation of Ser. No. 663,651, filed Mar. 4, 1976, and now abandoned.

This invention relates to certain organophosphorus compounds which are useful as stabilizers for polymer compositions. In a more particular sense it relates to a method for the preparation of such stabilizers.

The purpose of stabilizers is to prevent deterioration of the polymers during processing at high temperatures and also to permit the manufacture of products with increased intrinsic quality because of the enhancement of their resistance to thermal and light degradation during use. In addition, because of these enhanced properties, their versatility is increased and wider use is thereby made possible.

In the case of vinyl chloride polymers, several types of stabilizers have been found to be effective. These include various organic salts of cadmium, calcium, lead, zinc, barium, strontium, tin, magnesium and antimony, e.g. stearates, laurates, etc, mixed metal salts are especially useful. Dialkyl tin compounds are also effective. Despite the recognized ability of these compounds to confer some stability on these polymers, however, it is well known that the use of these metal salts, either alone or in combination with one another, does not in many instances provide the required resistance to deterioration. The performance of these metal stabilizers can be enhanced significantly by adding an organic phosphite to the vinyl chloride polymer composition.

Many such organic phosphites are available to serve this purpose. Among them are the bis-(alkylphenyl)pentaerythritol diphosphites which may have either (or both) the structures:

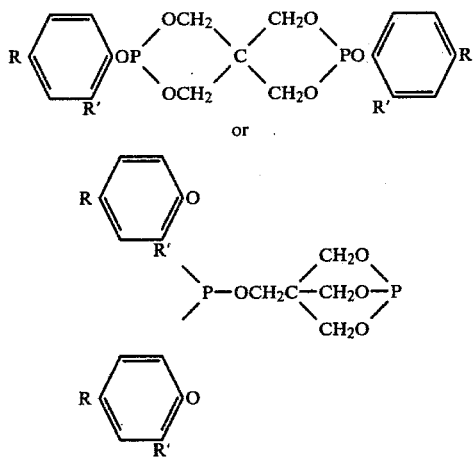

where R and R' are each alkyl of 3–10 carbon atoms. These phosphites provide eminently satisfactory performance because they tend to inhibit discoloration caused by high temperatures and also because they are themselves quite stable. That is, they are characterized by a relatively high degree of intrinsic stability, especially under conditions of high humidity. This quality is not normally characteristic of other organic phosphite stabilizers.

It will be noted that the above phosphites are "mixed" aryl aliphatic phosphites, i.e., the phosphorus atom is bound through oxygen both to aliphatic and to aromatic carbon atoms. Phosphites of this type have generally in the past been prepared by one of two methods: (1) the reaction of an aromatic dichlorophosphite with pentaerythritol, as alluded to in Baranauckas et al, U.S. Pat. No. 3,310,609; and (2) the reaction of a phenol with dichloropentaerythritol diphosphite, as shown in Gagliani, U.S. Pat. No. 3,192,243. Although these methods are useful they each suffer from certain disadvantages. Thus, method (1) requires the use of a solvent because of the very high melting point of pentaerythritol, 253° C. The solvent represents an additional expense and it must be removed and recovered, all of which adds up to a significant disadvantage.

Method (2), on the other hand, results in a product of less than satisfactory purity. A gas phase chromatogram of such a product shows as many as five compounds present in significant quantities and the product's melting curve is erratic, i.e., it melts (only partially) at a relatively low temperature, then resolidifies, then finally melts completely. Furthermore, it is quite waxy and has a tendence to "block", i.e., to congeal into hard, intractable lumps.

Friedman, U.S. Pat. No. 3,655,831, shows the reaction of 1,1,3-tris(4-hydroxyphenyl)propane with compounds of the structure

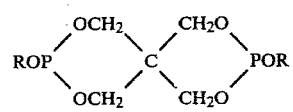

where R is alkyl, such as methyl, or aryl, such as phenyl. In most instances, however, the product is polymeric (because both reactants are multifunctional) and in any event the product inevitably is a complex mixture of several compounds. Friedman, U.S. Pat. No. 3,516,963 contains the same teaching.

U.K. Pat. No. 1,180,398 shows the reaction of a tri(substituted aryl)phosphite and an alcohol (which can be pentaerythritol) to form a product such as that which results from the process herein. As noted earlier, where pentaerythritol is one of the reactants its high melting point dictates the use of a solvent, which in turn presents processing and cost disadvantages.

The same objection is applicable to the process disclosed in Hechenbleikner, U.S. Pat. No. 2,847,443; viz., the reaction of an aromatic dichlorophosphite and pentaerythritol. Both such reactants as are required to prepare the product of the process of this invention are solids and a mutual solvent is indicated.

Rattenbury, U.S. Pat. No. 3,576,918, shows the reaction of diphenyl pentaerythritol diphosphite and hydrogenated bisphenol A, i.e., an aliphatic glycol. The product which results is entirely aliphatic, i.e., there is no aromatic group present at all. Furthermore, the product is a complex mixture because both reactants are multifunctional.

Thus, it will be seen that previously known processes have been characterized either by the production of a relatively impure product, which requires purification, or by the necessary use of a solvent. Either of these is an item of substantial expense.

The present invention comprises a process for preparing mixed aromatic-aliphatic phosphites comprising mixing a diphenyl pentaerythritol diphosphite or a dialkyl pentaerythritol diphosphite wherein the alkyl groups contain 1–4 carbon atoms, with an alkylphenol having the formula

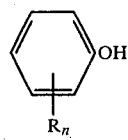

where R is alkyl of 3–10 carbon atoms and n is 1–3, and heating the resulting mixture so as to cause the formation of ROH and to remove such ROH by distillation. The product which results from this process is relatively pure, i.e., there is no substantial quantity of by-products; furthermore, the process is simple, requiring no solvent or unusual steps.

The substituent groups in the above pentaerythritol diphosphite most usually are phenyl. Diphenyl pentaerythritol diphosphite is readily available and its transesterification with phenols proceeds smoothly. The dimethyl compound likewise proceeds smoothly in such transesterifications and its use is limited only by its lesser availability and higher cost. The pentaerythritol diphosphite may be prepared by reaction of pentaerythritol with triphenyl phosphite or the appropriate trialkyl phosphite, or by reaction of dichloropentaerythritol diphosphite with phenol or a lower alcohol. The pentaerythritol diphosphite has either a spiro structure, e.g.

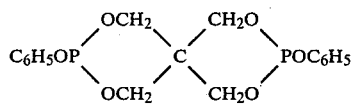

or a cage structure, e.g.,

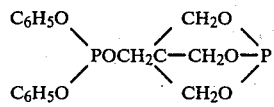

Generally, pentaerythritol diphosphite compositions are a mixture of the above two structures, in varying proportions depending upon the particular method of preparation. Similarly, the bis-(alkylphenyl)pentaerythritol diphosphites prepared by the process of this invention usually are a mixture of the spiro and cage structures illustrated above.

The alkylphenol used in the process preferably is a dialkylphenol because of the unusual thermal stability of the mixed aromatic-aliphatic phosphite which results upon reaction with the substituted pentaerythritol diphosphite. Especially preferred are those alkylphenols which contain alkyl groups such as tertiary butyl and 1,1-dimethylpropyl are commonly used. Illustrative species include 2,4-ditertiaryamylphenol, 2,4-ditertiarybutyl-phenol and 2,6-ditertiarybutylphenol.

Although the reaction will proceed in the absence of a catalyst it proceeds much more satisfactorily with an alkaline catalyst. Only a small amount is required to serve this purpose, i.e., from about 0.1 to about 5.0 percent of the total weight of the process mixture. The catalyst preferably is inorganic, and most preferably is an alkali or alkaline earth metal compound. Illustrative species include sodium hydroxide, sodium carbonate, potassium hydroxide, potassium carbonate, lithium carbonate, lithium hydroxide, sodium methylate, potassium methylate, sodium ethylate, calcium hydroxide and barium hydroxide.

The process conditions require merely heating the reactants to a temperature sufficient to permit distillation of the displaced phenol or lower alcohol, as the case may be. A suitable temperature in most instances ranges up to about 210° C. A solvent may be used and in some instances may afford certain advantages, but ordinarily it is preferred to carry out the reaction without a solvent. As the reaction proceeds, phenol (or a lower alcohol) is distilled from the product mixture; usually the last traces of such distillate are collected at reduced pressure.

The desired product is obtained as the residue; it is obtained as a relatively pure compound contaminated only by a small proportion of alkyl phenol. An excess of alkyl phenol is used in the reaction mixture so as to favor completion of the transesterification. The excess is of the order of about 5–25%, i.e., from about 2.1 to about 2.5 moles of alkyl phenol should be used per mole of pentaerythritol diphosphite.

The process of the invention is illustrated by the following example which should not be regarded as limiting in any respect.

EXAMPLE

A mixture of 267 g. (0.75 mol) of diphenyl pentaerythritol diphosphite, 371 g. (1.80 mols) of 2,4-ditertiarybutyl phenol and 8.5 g. of sodium methylate is heated with stirring at reduced pressure for 10 hours. During this time the temperature is increased and the pressure decreased gradually to 190C./5 mm. A total of 140 g. (99% of the theoretical amount) of distillate, identified by its set point (38°–40° C.) as phenol, is obtained by distillation as the reaction proceeds. Further heating to a final temperature of 210° C./5 mm. removes the unreacted 2,4-ditertiarybutyl phenol leaving 450 g. of a product, bis-(2,4-ditertiarybutylphenyl)pentaerythritol diphosphite, shown by gas phase chromotography to have 2.0% of 2,4-ditertiarybutyl phenol. Its acid number is 0.02 and its melting point is 135°–150° C.

The efficiency as polymer additives of the diphosphite products prepared herein is shown by the results of a test whereby the stabilization of polypropylene, even after repeated extrusion at high temperatures, is noted. The compositions tested are as follows:

| Parts | Component |
|---|---|
| 100 | Polypropylene |
| 0.05 | Calcium stearate |
| 0.10 | Irganox 1010* |

*Tetrakis methylene 3-(3',5'-ditertiarybutyl-4'-hydroxyphenyl) propionate methane to which are added the diphosphites as shown in Table I. The test compositions are extruded at 475° F. from a screw-fed chamber at 76 RPM and a back pressure of 750 psi. The extruded material is extruded three more times, under the same conditions, and then separate samples are extruded a fifth time at 475° F. and 525° F., at 70 RPM and 1000 psi back pressure. After the first and fifth extrusions the stabilizing effectiveness of the diphosphite additive is determined by means of a heat aging test. The extruded test compositions, in the form of 25-mil thick samples, are heated at 150° C. in an oven until failure, as noted by sudden crazing, cracking and- /or embrittlement. The time, in hours of heating required for such failure, is taken as a measure of the stability of the sample. Data are shown in Table I.

TABLE I

| Diphosphite Stabilizer | 1st Extrusion 475° F. | 5th Extrusion | |
|---|---|---|---|
| | | 475° F. | 525° F. |
| 1. 0.07 part of bis-(2,4-ditertiarybutyl-phenyl)pentaerythritol diphosphite | 1340 | 1267 | 1339 |
| 2. 0.07 part of bis-(2,6-ditertiarybutyl-phenyl) pentaerythritol diphosphite | 1414 | 1273 | 1327 |

It will be noted that the samples are substantially unchanged, with respect to deterioration on heating at 150° C., even after five extrusions at high temperature.

Additional test data showing the efficiency of the diphosphite products herein are contained in Table II. The data shows the melt index of a test composition immediately after each of five extrusions at 475° F. and 525° F., i.e. a total of ten extrusions per test composition. The melt indexes are measured in accordance with the requirements of condition L of ASTM D1238, i.e., the weight in grams of the test composition which flows through an orifice of specified diameter in ten minutes. The test compositions are those set out in Table I.

TABLE II

| Diphosphite Stabilizer | Temp. | Extrusion | | | | |
|---|---|---|---|---|---|---|
| | | 1 | 2 | 3 | 4 | 5 |
| 3. As in 1. (Table I) | 475° F. | 3.2 | 3.2 | 3.2 | 3.5 | 3.7 |
| | 525° F. | 3.2 | 3.3 | 3.5 | 4.0 | 3.8 |
| 4. As in 2. (Table II) | 475° F. | 3.1 | 3.1 | 3.4 | 3.5 | 3.7 |
| | 525° F. | 3.3 | 3.5 | 3.7 | 3.4 | 3.8 |

A direct comparison of two polypropylene compositions, one (No. 1) containing 0.07 part of bis-(2,4-ditertiarybutylphenyl)pentaerythritol diphosphite, is shown in Table III. Each of the two compared compositions contains the following ingredients:

| Parts | Component |
|---|---|
| 100 | Polypropylene |
| 0.05 | Calcium stearate |
| 0.08 | Irganox 1010 |

The test samples are extruded five times at 525° F. and the melt index determined after each extrusion.

TABLE III

| Diphosphite Stabilizer | Extrusion | | | | |
|---|---|---|---|---|---|
| | 1 | 2 | 3 | 4 | 5 |
| 5. None | 8.8 | 10.8 | 12.6 | 16.4 | 20.0 |
| 6. As in 1. (Table I) | 4.8 | 4.9 | 5.7 | 6.0 | 9.0 |

All parts herein are by weight unless otherwise expressly stated.

We claim:

1. A polymer composition comprising polypropylene and a minor proportion, sufficient to stabilize said polymer, of a di-(dialkylphenyl)pentaerythritol diphosphite.

2. The polymer composition of claim 1 wherein the di(dialkylphenyl)pentaerythritol diphosphite is a di-(2,4-dialkylphenyl)pentaerythritol diphosphite.

3. The polymer composition of claim 1 wherein the di(dialkylphenyl)pentaerythritol diphosphite is a di-(2,4-dibutylphenyl)pentaerythritol diphosphite.

4. The polymer composition of claim 1 wherein it additionally contains a minor proportion, sufficient to stabilize said polymer, of a phenolic antioxidant.

5. The polymer composition of claim 4 wherein the phenolic antioxidant is a phenolic ester.

6. The polymer composition of claim 5 wherein the phenolic antioxidant is an aliphatic ester of 3(3',5'-ditertiarybutyl-4'-hydroxyphenyl)propionic acid.

7. A polymer composition comprising an olefin polymer normally susceptible to thermal degradation and a minor proportion, sufficient to stabilize said polymer, of a di-(alkylphenyl)pentaerythritol diphosphite prepared by mixing a diphenylpentaerythritol diphosphite or a dialkylpentaerythritol diphosphite wherein the alkyl groups contain 1–4 carbon atoms, with an alkylphenol having the formula:

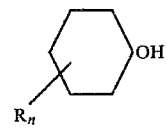

where R is alkyl of 3–10 carbon atoms and n is 2–3, and heating the resulting mixture so as to cause the formation of phenol or a lower alcohol, as the case may be, and to remove such phenol or lower alcohol by distillation.

8. The polymer composition of claim 7 wherein the alkylphenol is 2,4-ditertiarybutyl phenol.

* * * * *